United States Patent [19]
Kohl et al.

[11] Patent Number: 4,749,732
[45] Date of Patent: Jun. 7, 1988

[54] HAIR CARE COMPOSITION CONTAINING MODIFIED AMINOALKYL SUBSTITUTED POLYDIORGANOSILOXANE

[75] Inventors: Gretchen S. Kohl; Thomas H. Lane, both of Midland, Mich.

[73] Assignee: Dow Corning Corporation, Midland, Mich.

[21] Appl. No.: 294

[22] Filed: Jan. 2, 1987

[51] Int. Cl.$^4$ ............................................... C08L 1/26
[52] U.S. Cl. ........................................ 524/43; 524/44; 524/46; 524/47; 524/55; 524/58; 524/375; 524/173; 524/588; 528/26; 528/38; 424/70
[58] Field of Search ...................... 424/70; 528/26, 38; 524/43, 44, 46, 55, 47, 58, 375, 588, 173

[56] References Cited

U.S. PATENT DOCUMENTS

| | | | |
|---|---|---|---|
| 3,033,815 | 5/1962 | Pike et al. | 260/46.5 |
| 3,317,577 | 5/1967 | Ryan | 260/448.2 |
| 4,507,455 | 3/1985 | Tangney et al. | 528/26 |
| 4,559,227 | 12/1985 | Chandra et al. | 424/70 |
| 4,563,347 | 1/1986 | Starch | 424/70 |
| 4,620,878 | 11/1986 | Gee | 106/287.15 |

FOREIGN PATENT DOCUMENTS 2157168 12/1984 United Kingdom .
2143434 10/1985 United Kingdom .

Primary Examiner—Melvyn I. Marquis
Attorney, Agent, or Firm—Marc C. Pawl

[57] ABSTRACT

Hair care uses of polydiorganosiloxanes containing aminoalkyl groups modified by alkoxycarbonylalkyl substituents are described. The modified aminoalkyl silicones exhibit improved deposition on hair and can be formulated into shampoos, conditioners, rinses, creams, gels, aerosol foams or sprays, and permanent waving products.

17 Claims, No Drawings

HAIR CARE COMPOSITION CONTAINING MODIFIED AMINOALKYL SUBSTITUTED POLYDIORGANOSILOXANE

BACKGROUND OF THE INVENTION

This invention relates to the use of modified aminoalkyl substituted polydiorganosiloxane in hair care compositions such as conditioners and shampoos. More specifically, the invention relates to compositions and methods for treating hair with polydiorganosiloxane containing aminoalkyl groups modified by alkoxycarbonylalkyl substituents.

Aminoalkyl substituted polydiorganosiloxanes are well known copolymers which are typically composed of dimethylsiloxane units and aminoalkylmethylsiloxane units. For example, Starch, U.S. Pat. No. 4,563,347, Jan. 7, 1986. describes a copolymer represented by the formula $$(CH_3)_3SiO[CH_3SiO]_2[(CH_3)_2SiO]_{96}Si(CH_3)_3$$
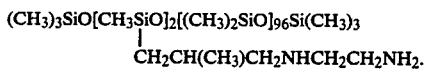

Such copolymers are further described in the *CTFA Cosmetic Ingredient Dictionary.* 3rd edition, 1982, published by The Cosmetic. Toiletry and Fragrance Association. Inc. 1133 Fifteenth Street NW Washington D.C. (USA) under the nomenclature amodimethicone and trimethylsilylamodimethicone.

The use of aminoalkyl substituted polydiorganosiloxane in hair care compositions is also well known. For instance, Starch. U.S. Pat. No. 4,563,347, teaches using these copolymers in hair conditioning compositions to improve combing and feel characteristics. Similarly. Grollier et al., UK patent application Nos. 2,157,168 and 2.143.434, Oct. 23, 1985 and Feb. 13, 1985 respectively, teach using the aminoalkyl substituted polydiorganosiloxanes with other components in hair care compositions which may be formulated as a shampoo, a rinsed or non-rinsed lotion, a restructuring composition, a composition for blow drying, or a composition for permanent waving.

The aminoalkyl substituents are credited with providing the copolymers with cationic sites that make the polymer more substantive to hair than nonsubstituted polydimethylsiloxane. However, the chemical reactivity of the aminoalkyl groups may also present a problem in regard to compatibility with other common components of hair care formulations. Compatibility problems may be observed especially with anionic surfactants. Tangney et al., U.S. Pat. No. 4,507,455, Mar. 26, 1985, describe a method of modifying the chemical reactivity of aminoalkyl substituents of polydiorganosiloxane by reacting the polymer with a monocarboxylic acid anhydride to acylate the amine groups and thus convert them to amides. While acylation was effective to improve compatibility, it has also been found to reduce the substantivity of the polymer to hair so that the utility of the polymers in hair care compositions is limited. It is a purpose of the present invention to provide hair care compositions containing a conditioning silicone polymer which has the advantage of being highly substantive to hair but at the same time has a more moderate chemical reactivity with correspondingly reduced compatibility problems.

Aminoalkyl substituted silanes and polydiorganosiloxanes have been reacted with acrylate esters to provide silanes and polydiorganosiloxanes in which the amine is modified by addition of an alkoxycarbonylalkyl group to the nitrogen atom. For example, the reaction is illustrated as follows for methylacrylate addition to an aminopropyl substituent of a polydiorganosiloxane.

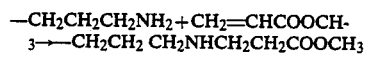

More specifically, Pike et al., U.S. Pat. No. 3,033,815, May 8, 1962, describe the reaction of methylacrylate with a silicone copolymer of 90 percent dimethylsiloxane units and 10 percent delta-aminobutylmethylsiloxane units. The resulting silicone is described as containing delta-(N-2-carbomethoxyethyl)aminobutylmethylsiloxane units. Pike et al. teach that these compounds find use as sizes for fibrous materials, particularly fibrous glass materials employed in combination with thermosetting resins and that the monomeric and polymeric compounds can also be employed as adhesives or as flocculation agents.

Similarly, Ryan, U.S. Pat. No. 3,317,577, May 2, 1967, describes the addition of methylacrylate to silanes and organosiloxanes having diaminoalkyl groups such as N-(2-aminoethyl)-3-aminopropyl groups ($-CH_2CH_2CH_2NHCH_2CH_2NH_2$). Ryan teaches that the materials are useful as binding agents for binding pigments to glass fabric and other siliceous surfaces, that they are useful as priming agents on metallic surfaces for securing adhesion of subsequently applied resin coatings, that they are useful as binding agents in the preparation of glass fiber polyester laminates, and that fluids prepared from the polymers and copolymers are also of interest as heat exchange agents and for further reaction to modify organic materials.

Neither Pike et al. nor Ryan suggest that their modified aminoalkyl substituted polydiorganosiloxanes are useful in hair care compositions. The use of these materials in hair treating compositions is believed to be novel.

SUMMARY OR THE INVENTION

The present invention relates to a hair treating composition comprising (a) from 0.01 to 10 parts by weight of an organopolysiloxane represented by the formula

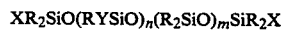

wherein R denotes a monovalent hydrocarbon radical having 1 to 6 carbon atoms; X denotes —OH, —OR, Y, or R; Y denotes a substituent of the formula

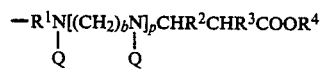

wherein $R^1$ denotes an alkylene radical having 3 to 6 carbon atoms, $R^2$ denotes a hydrogen atom, phenyl, or an alkyl radical of 1 to 6 carbon atoms, $R^3$ denotes a hydrogen atom or methyl radical, and $R^4$ denotes an alkyl radical having 1 to 6 carbon atoms, b has a value of 2, 3, or 4, p has a value of 0, 1, or 2, and Q denotes a hydrogen atom. an alkyl radical having 1 to 4 carbon atoms, or a radical of the formula —$CHR^2CHR^3COOR^4$ wherein $R^2$, $R^3$, and $R^4$ have the same meanings as defined above; m has an average value from 10 to 600: n has an average value of 0 to 100 with the proviso that when n is 0, X denotes Y and (b) from 50 to 100 parts by weight of a physiologically acceptable carrier. The invention also relates to the method of conditioning hair which comprises contacting hair with the treating composition defined above.

DETAILED DESCRIPTION OF THE INVENTION

In the present invention, certain modified aminoalkyl substituted polydiorganosiloxanes are used in hair treating compositions such as conditioners. rinses, and shampoos. The useful polydiorganosiloxanes are represented by the formula $$XR_2SiO(RYSiO)_n(R_2SiO)_mSiR_2X \quad I$$

wherein R denotes a monovalent hydrocarbon radical having 1 to 6 carbon atoms. The organic groups denoted by R in formula I may be alkyl groups such as methyl, ethyl, or hexyl, alkenyl groups such as vinyl or allyl; or an aryl group such as phenyl. The diorganosiloxane polymers most useful in this invention are predominantly methyl substituted polymers wherein at least 90 percent of R radicals in the formula are methyl groups. It is most preferred to use polydimethylsiloxanes wherein essentially all R radicals are methyl groups.

In formula I, X denotes —OH, —OR, Y, or R where R has the same meaning described above and Y denotes a modified aminoalkyl substituent. Thus the polymer may be terminated by a hydroxyl group, a hydrocarbonoxy group, or a triorganosiloxane unit. When n is not zero so that the polymer has pendant modified aminoalkyl substituents, it is preferred that the polymer be terminated by triorganosiloxane units such as dimethylvinylsiloxane units, dimethylphenylsiloxane units or trimethylsiloxane units, with trimethylsiloxane units being most preferred. When n is zero, X denotes a modified aminoalkyl substituent so that useful polymers have the formula $$YR_2SiO(R_2SiO)_mSiR_2Y \quad II$$

wherein R has the same meaning as described above.

In formula I and II, Y denotes a modified aminoalkyl substituent represented by the formula

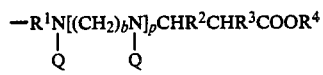

wherein $R^1$ denotes an alkylene radical having 3 to 6 carbon atoms. Alkylene radical, $R^1$, may be a straight chain radical such as trimethylene, tetramethylene, or hexamethylene or a branched radical such as 2-methylpropylene, —$CH_2CH(CH_3)CH_2$—. $R^2$ denotes a hydrogen atom, phenyl, or an alkyl radical of 1 to 6 carbon atoms such as methyl, isopropyl, butyl, or hexyl, $R^3$ denotes a hydrogen atom or a methyl radical. $R^4$ denotes an alkyl radical having 1 to 6 carbon atoms, for example, methyl, ethyl, propyl, pentyl, or isobutyl. In the modified aminoalkyl substituent, b may have a value of 2, 3, or 4 and p may have a value of 0, 1, or 2. Q denotes a hydrogen atom, an alkyl radical having 1 to 4 carbon atoms, or a radical of the formula —$CHR^2CHR^3COOR^4$ wherein R2 R3 and R4 have the same meanings as defined previously. Alkyl radicals having 1 to 4 carbon atoms include methyl, ethyl, isopropyl, and butyl. Generally, silicones are preferred wherein Q denotes a hydrogen atom or a radical of the formula —$CHR^2CHR^3COOR^4$.

According. to the present invention. useful modified aminoalkyl substituents include, for example —$CH_2CH(CH_3)CH_2NHCH_2CH_2NHCH_2CH_2COOCH_3$,
—$CH_2CH_2CH_2NHCH_2CH_2COOCH_3$,
—$CH_2CH_2CH_2N(CH_2CH_3)CH_2CH_2COOCH_3$,
—$CH_2CH_2CH_2NHCH_2CH_2NHCH_2CH_2COOCH_2CH_3$,
—$CH_2CH_2CH_2N(CH_2CH_2COOCH_3)_2$,
—$CH_2CH(CH_3)CH_2NHCH_2CH_2N(CH_2CH_2COOCH_3)_2$,

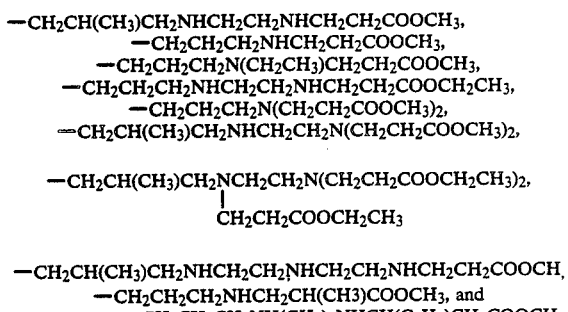

—$CH_2CH(CH_3)CH_2NHCH_2CH_2NHCH_2CH_2NHCH_2CH_2COOCH$,
—$CH_2CH_2CH_2NHCH_2CH(CH_3)COOCH_3$, and
—$CH_2CH_2CH_2NH(CH_2)_3NHCH(C_6H_5)CH_2COOCH_2$.

The modified aminoalkyl substituted polydiorganosiloxane may vary widely in viscosity and degree of polymerization. In formula I for example, m may vary from an average value of 10 to 600 and n may vary from an average value of 0 to 100. However, polymers wherein m has an average value from 40 to 400 and n has an average value from 1 to 60 with the ratio of n to m being less than or equal to 0.15 are generally preferred for use in the hair treating compositions of this invention. Such polymers are preferred because they have viscosities which allow more easy formulation with other components typically used in hair treating compositions and because they have sufficient amino functionality to provide substantivity to hair.

Methods of preparing the modified aminoalkyl substituted polydiorganosiloxanes that are employed in the hair treating compositions according to this invention are known in the art. For example U.S. Pat. Nos. 3,033,815 and 3,317,577, which are hereby incorporated by reference, teach methods whereby aminoalkyl substituted polydimethylsiloxanes are reacted with acrylate esters to prepare polymers useful in the present invention.

The modified aminoalkyl substituted polydiorganosiloxane must be dissolved or dispersed in a carrier to be useful for treating hair. Typically, useful hair treating compositions will contain from 0.01 to 10 parts of silicone polymer diluted in 50 to 100 parts of a carrier liquid. Since the carrier serves only to dilute the silicone polymer to allow uniform application of appropriately small quantities, any carrier that is physiologically acceptable for use on the human body may be used. For example, the silicone polymer can be dissolved in organic solvents including chlorinated alkanes such as 1,1,1-trichloroethane and methylene dichloride, alcohols such as ethanol and isopropanol, and polyols such as ethylene glycol and propylene glycol.

The silicone polymer can also be used to treat hair in an aqueous dispersion or emulsion. Treating hair with an emulsion of silicone in water is an especially preferred embodiment of the present invention. Aqueous emulsions of silicone polymer may be prepared by high shear mixing of the polymer in water using a suitable emulsifying surfactant as is well known in the art. Microemulsions of silicone polymers in water are also highly preferred for use in the present invention. Microemulsions of modified aminoalkyl substituted polydiorganosiloxane can be prepared by the method described in U.S. Pat. No. 4,620,878 which describes generally the preparation of emulsions of silicones containing polar substituents.

Depending on the specific hair treating application, the compositions of this invention may be thickened or unthickened creams, gels, aerosol foams, or sprays. Suitable thickeners include, among others, sodium alginate, gum arabic, polyoxyethylene, cellulose derivatives such as methylcellulose, hydroxymethylcellulose, hydroxyethylcellulose, hydroxypropylcellulose, hydroxypropylmethylcellulose, guar gum or its derivatives, starch and starch derivatives such as hydroxyethylamylose and starch amylose, locust bean gum, electrolytes such as NaCl, saccharides such as fructose and glucose, and derivatives of saccharides such as PEG-120 methyl glucose dioleate. The hair treating compositions may be applied in the form of shampoo; rinsing products to be applied after shampooing, before or after tinting or bleaching, and before or after permanent waving or straightening; products for setting or brushing; conditioning compositions, restoring compositions; and compositions for permanent-waved hair.

The types of hair treating compositions encompassed by the present invention is further illustrated, but not limited, by specific reference to the following preferred embodiments. Hair treating compositions of this invention may form a shampoo, in which case, the compositions contain a cleansing surfactant in addition to the silicone polymer and carrier. The concentration of cleansing surfactant can range from about 2 to 40 parts by weight per 100 parts of total composition. Cleansing surfactants selected from the group consisting of anionic surfactants, nonionic surfactants, and amphoteric surfactants are well known for use in shampoo formulations. For example, the anionic, nonionic and amphoteric surfactants useful as cleansing agents in shampoos are further described in U.S. Pat. No. 4,559,227, which is hereby incorporated by reference.

Typical cleansing surfactants include the anionics such as the sodium, ammonium, or triethanolamine salts of lauryl sulfate and lauryl ether sulfate; the nonionics such as fatty acid alkanolamides like lauric acid diethanolamide; and the amphoterics such as N-cocamidopropyl dimethyl glycine. Generally the anionic surfactants, especially the sodium, ammonium, and triethanolamine salts of lauryl sulfate, are preferred since they provide richer, denser foams than other types of cleansing surfactants at comparable concentrations.

In another embodiment of the present invention, the hair treating composition may form a conditioning product for application to hair after shampooing. The hair is typically rinsed in running water after treating with the conditioning product. Conditioners facilitate combing out hair and impart softness and suppleness to the hair. Conditioning products may also contain other components such as thickeners and auxiliary conditioning compounds. Auxiliary conditioning agents may be used to provide further improved conditioning benefits such as antistatic characteristics. Auxiliary conditioning agents useful in the compositions of this invention include the organic cationic compounds and polymers such as stearyldimethylbenzylammonium chloride, quaternary nitrogen derivatives of cellulose ethers, and homopolymers and copolymers of dimethyldiallylammonium chloride, and other quaternary ammonium compounds which are known for use in hair conditioning formulations.

In another embodiment of the present invention, the hair treating composition may be in the form of a product for permanent waving hair. The conventional technique for these permanent waves consists in applying, in a first stage, a composition containing a reducing agent and then, after having rinsed the hair if appropriate, applying a composition containing an oxidizing agent. According to the present invention, at least one of the two compositions is a hair treating composition containing modified aminoalkyl substituted polydiorganosiloxane and carrier in addition to the reducing or oxidizing agent.

One advantage of the hair treating compositions of this invention is the increased amount of silicone polymer deposited on the hair in comparison to the amount of silicone deposited when hair is treated by prior art silicone materials. Also, the hair treating compositions of the invention are more easily formulated with other hair care components because of the reduced reactivity of the modified aminoalkyl substituted polydiorganosiloxane with other components.

The following examples are presented to illustrate the invention to those skilled in the art and should not be construed as limiting the invention, which is properly delineated in the appended claims. All proportions by parts or percents are by weight unless otherwise stated.

EXAMPLE 1

This example shows that aminoalkyl substituted polydiorganosiloxane which has been modified by reaction with methylacrylate is useful to condition hair. Also, the combing improvement provided by the methylacrylate modified silicone is compared to the improvement provided by the unmodified silicone and to silicone modified by reaction with acetic anhydride.

Hair treating compositions suitable for use as hair conditioners were prepared by making an emulsion of the various silicone polymers in water. Stock emulsions were prepared by mixing 4.4 g of isolaureth-6 ($C_{12}H_{25}(OCH_2CH_2)_6OH$ sold under the trademark TERGITOL TMN-6 by Union Carbide Corp., Danbury, Conn.), 12.1 g of octoxynol-40 ($C_8H_{17}C_6H_4(OCH_2CH_2)_{40}OH$ sold under the trademark TRITON X-405 by Rohm and Haas Company, Inc., Philadelphia, Pa.), and 76.1 g of water and then adding 50 g of silicone polymer while homogenizing the mixture on a colloid mill. The stock emulsions contained 35% silicone, 11.6% emulsifying surfactants, and 53.4% water. Portions of each stock emulsion were diluted to 0.25% silicone with additional water to provide baths for treating hair in the following tests.

The silicone polymers tested generally conformed to the average formula

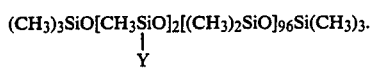

The specific structure of the Y substituents for the polymers in each emulsion tested is shown in Table 1. Silicone Emulsions A and B illustrate the present invention while Silicone Emulsions C, D, and E represent the prior art and are presented for comparison purposes.

TABLE 1

| Silicone Emulsion | Y |
|---|---|
| A | $-CH_2CH(CH_3)CH_2NHCH_2CH_2NHCH_2CH_2COOCH_3$ |
| B* | $-CH_2CH(CH_3)CH_2NCH_2CH_2NCH_2CH_2COOCH_3$ with Q, Q substituents |
| C | $-CH_2CH(CH_3)CH_2NHCH_2CH_2NH_2$ |
| D | $-CH_2CH(CH_3)CH_2NHCH_2CH_2NHCCH_3$ (with =O) |
| E | $-CH_2CH(CH_3)CH_2NCH_2CH_2NHCCH_3$ with $O=CCH_3$ substituent (with =O) |

*Q groups are half hydrogen and half methoxycarbonylethyl groups of the formula $-CH_2CH_2COOCH_3$ The conditioning efficacy of each silicone emulsion was evaluated by measuring the force required to comb both wet and dry hair after it had been treated with the compositions. Hair tresses were made by assembling 12 g bundles of 30 cm natural brown, virgin European hair and binding the root ends in wax. All reported combing results are averages for three tresses treated with each composition.

Combing forces were measured on an INSTRON strain gauge adapted with a hard rubber comb. The combing force was recorded as the comb was moved down through the tress which was attached to the end of a stationary load cell. The average combing load (ACL) was determined by integrating the total combing force over the entire tress length and is reported in grams. Four combing strokes were conducted for each treatment condition of a tress and averaged to obtain more representative values.

Tresses were washed with a conventional shampoo and dried at least 18 hr under ambient conditions prior to initial combing force measurement in the dry/untreated state. Tresses were then soaked in water for 12-30 minutes and combing forces measured again in the wet/untreated state. Between each of the four wet combing strokes, the hair was dipped three times in water to uniformly retangle the hair. Tresses were then treated by dipping for 30 sec. in a 200 g bath of silicone emulsion (0.25% silicone solids). The tresses were rinsed for 30 sec. in 40° C. running tap water and the combing forces measured in the wet/treated state. Combing forces were measured again in the dry/treated state after the hair had dried for at least 18 hr under ambient conditions. Combs were changed between treated and untreated tresses, and a new comb was used for each treatment material.

The percent change in ACL was calculated as $$\% \text{ Change} = \frac{ACL_T - ACL_U}{ACL_U} \times 100$$

where $ACL_T$ is the average combing load for the treated tress and $ACL_U$ is the average combing load for the untreated tress. Percent change values are shown in table 2 for both the dry and the wet state.

TABLE 2

| Silicone Emulsion | Percent Change in ACL | |
|---|---|---|
| Treatment | Dry | Wet |
| A | −37 | −69 |
| B | −35 | −53 |
| C | −65 | −66 |
| D | −35 | −63 |
| E | −10 | +1 |

EXAMPLE 2

This example shows an additional type of methylacrylate modified aminoalkyl substituted polydiorganosiloxane that is useful to condition hair. Also, the combing improvement provided by the methylacrylate modified silicone is compared to the improvement provided by the unmodified silicone.

Hair treating compositions were prepared by making an emulsion of the various silicone polymers in water according to the procedure described in Example 1. The silicone polymers tested generally conformed to the average formula

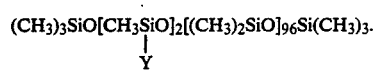

The specific structure of the Y substituents for the polymers in each emulsion tested is shown in Table 3. Silicone Emulsion F illustrates the present invention while Silicone Emulsions G and H represent the prior art and are presented for comparison purposes.

TABLE 3

| Silicone Emulsion | Y |
|---|---|
| F | $-CH_2CH(CH_3)CH_2N(CH_3)CH_2CH_2COOCH_3$ |
| G | $-CH_2CH(CH_3)CH_2NHCH_3$ |
| H | $-CH_2CH(CH_3)CH_2NHCH_2CH_2NH_2$ |

The conditioning efficacy of each silicone emulsion was evaluated by measuring the force required to comb dry hair after it had been treated with the compositions. The hair tresses were treated and combing forces measured by the same procedures described in Example 1. The percent change in average combing load between treated and untreated tresses is shown in table 4.

TABLE 4

| Silicone Emulsion Treatment | Percent Change in ACL Dry |
|---|---|
| F | −15 |
| G | −52 |
| H | −12 |

EXAMPLE 3

This example demonstrates the substantivity of the silicones of this invention on hair and compares their substantivity to that of prior silicones used in hair care.

Clippings of the treated hair tresses from Example 1 were analyzed to determine the amount of silicone bound or adsorbed on the hair. In addition, after initial clippings were removed, the tresses were washed with 0.6 g of conventional shampoo for 60 sec., blow dried, and additional clippings taken for analysis. Additional washing steps were performed with further clippings taken for analysis after the 3rd and 5th wash.

Hair clippings were analyzed by atomic absorption determination of silicon after the hair had been digested with papain enzyme. The digested hair samples were extracted in acidified methyl isobutyl ketone for analysis. The results are presented as parts per million (ppm) of total silicon in Table 5.

The data in Table 5 demonstrates that the acrylate modified silicones surprisingly were deposited more effectively on hair than the other materials, yet they were effectively removed after 1 to 3 washings so that undesirable buildup on the hair did not occur.

TABLE 5

| Silicone Treatment | Silicon Detected (ppm) Number of Washes After Treatment | | | |
|---|---|---|---|---|
|  | 0 | 1 | 3 | 5 |
| A | 1460 | 430 | 260 | 270 |
| B | 1060 | 180 | 160 | 180 |
| C* | 580 | 350 | 270 | 270 |
| D* | 550 | 190 | 130 | 140 |
| E* | 180 | 100 | 130 | 100 |
| Untreated Hair | 180 | 110 | 60 | 100 |

*Comparison examples, not encompassed by the present invention

EXAMPLE 4

This example illustrates the preparation of a shampoo formulation within the hair treating compositions of the present invention. The shampoo employs ammonium lauryl sulfate as an anionic cleansing surfactant.

A shampoo was prepared by first heating a solution of 9 g of ammonium lauryl sulfate in 61 g of water to 80° C. A separate mixture of 6 g of lauric acid diethanolamide and 2 g of the silicone polymer from Silicone Emulsion A of Example 1 (a methylacrylate modified aminoalkyl substituted polydimethylsiloxane) was heated to 80° C. and then added with stirring to the aqueous surfactant solution. A clear solution resulted which was thickened by addition of 2.5 g of PEG-120 methyl glucose dioleate (a methyl glucoside derivative with two polyoxyethylene substituent groups containing a total of 120 oxyethylene units). The thickener was melted and then mixed into the shampoo composition. After cooling, the pH of the composition was adjusted to 6.8 with 25% aqueous citric acid solution and sufficient additional water added to make 100 g of shampoo composition.

EXAMPLE 5

This example illustrates the preparation of a shampoo formulation within the hair treating compositions of the present invention. The shampoo employs a mixture of ammonium lauryl sulfate (anionic) and N-cocamidopropyl dimethyl glycine (amphoteric) as a cleansing surfactant.

A mixture of 5.25 g of N-cocamidopropyl dimethyl glycine, 4 g of lauric acid diethanolamide, 2 g of the silicone polymer from Silicone Emulsion A of Example 1, and 12.25 g of water was heated to 80° C. and added to a similarly heated solution of 5.25 g of ammonium lauryl sulfate in 24.25 g of water. After cooling, an additional 43 g of water was added. The pH was adjusted to 5.5–6.0 with 25% aqueous citric acid. The solution was thickened by adding NaCl and sufficient additional water was added to make 100 g of shampoo composition.

EXAMPLE 6

This example illustrates the improved skin toxicological characteristics of the silicones used in the hair treating compositions of the present invention. The silicone polymers described in Example 1 were tested for acute eye and dermal irritation in rabbits. The results are presented in Table 6.

TABLE 6

| Silicone Polymer | Acute Eye Irritation | Acute Dermal Irritation |
|---|---|---|
| A | slight irritant | slight irritant |
| B | slight redness | non-irritating |
| C* | moderate irritant | moderate to severe irritation |
| D* | moderate irritant | moderate irritation |
| E* | slight redness | non-irritating |

*Comparison examples, not encompassed by the present invention

That which is claimed is:
1. A hair treating composition comprising
(a) from 0.01 to 10 parts by weight of a polydiorganosiloxane represented by the formula $XR_2SIO(RYSiO)_n(R_2SiO)_mSiR_2X$

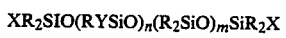

wherein R denotes a monovalent hydrocarbon radical having 1 to 6 carbon atoms; X denotes —OH, —OR, Y, or R; Y denotes a substituent of the formula $-R^1N[(CH_2)_bN]_pCHR^2CHR^3COOR^4$
$\phantom{-R^1N[(CH_2)_bN]_p}|\phantom{CHR^2CHR^3COO}|$
$\phantom{-R^1N[(CH_2)_bN]_p}Q\phantom{CHR^2CHR^3COO}Q$

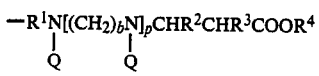

wherein $R^1$ denotes an alkylene radical having 3 to 6 carbon atoms, $R^2$ denotes a hydrogen atom, phenyl, or an alkyl radical of 1 to 6 carbon atoms, $R^3$ denotes a hydrogen atom or methyl radical, and $R^4$ denotes an alkyl radical having 1 to 6 carbon atoms, b has a value of 2, 3 or 4, p has a value of 0, 1, or 2, and Q denotes a hydrogen atom, an alkyl radical having 1 to 4 carbon atoms, or a radical of the formula $-CHR^2CHR^3COOR^4$ wherein $R^2$, $R^3$, and $R^4$ have the same meanings as defined above; m has an average value from 40 to 600; n has an average value of 0 to 100 with the proviso that when n is 0, X denotes Y and (b) from 50 to 100 parts by weight of a physiologically acceptable carrier.

2. The hair treating composition according to claim 1 wherein R denotes methyl and p has a value of 1.

3. The hair treating composition according to claim 2 wherein X denotes methyl, n has an average value of 1 to 100, and Y denotes a substituent of the formula

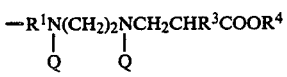

4. The hair treating composition according to claim 3 wherein the polydiorganosiloxane is represented by the formula

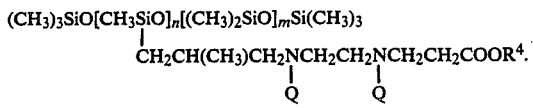

5. The hair treating composition according to claim 4 wherein the polydiorganosiloxane is represented by the formula

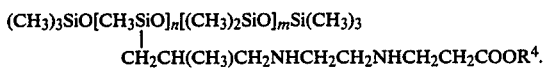

6. The hair treating composition according to claim 4 wherein about 50 percent of the substituents denoted by Q are $-CH^2CH^2COOR^4$ and the remainder are hydrogen.

7. The hair treating composition according to claim 4 wherein m has an average value from 40 to 400. n has an average value from 1 to 60, and ratio of n to m is less than or equal to 0.15.

8. The hair treating composition according to claim 7 wherein the carrier is water.

9. The hair treating composition according to claim 1 which further comprises from 2 to 40 parts by weight of a cleansing surfactant selected from the group consisting of anionic surfactants, nonionic surfactants, and amphoteric surfactants.

10. The hair treating composition according to claim 9 wherein the cleansing surfactant is an anionic surfactant.

11. The hair treating composition according to claim 10 wherein the anionic surfactant is a sodium, ammonium, or triethanolamine salt of lauryl sulfate.

12. The method of conditioning hair which comprises contacting hair with the treating composition defined in claim 1.

13. The method of conditioning hair which comprises contacting hair with the treating composition defined in claim 9.

14. The hair treating composition according to claim 4 wherein the polydiorganosiloxane is represented by the formula

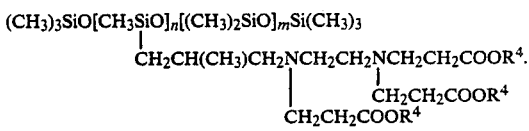

15. A hair treating composition comprising
(a) from 0.01 to 10 parts by weight of a polydiorganosiloxane represented by the formula $XR_2SiO(RYSiO)_n(R_2SiO)_mSiR_2X$ wherein R denotes a monovalent hydrocarbon radical having 1 to 6 carbon atoms; X denotes $-OH$, $-OR$, Y, or R; Y denotes a substituent of the formula

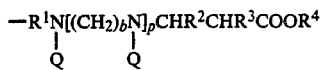

wherein $R^1$ denotes an alkylene radical having 3 to 6 carbon atoms, $R^2$ denotes a hydrogen atom, phenyl, or an alkyl radical of 1 to 6 carbon atoms, $R^3$ denotes a hydrogen atom or methyl radical, and $R^4$ denotes an alkyl radical having 1 to 6 carbon atoms, b has a value of 2, 3 or 4, p has a value of 0, 1, or 2, and Q denotes an alkyl radical having 1 to 4 carbon atoms, or a radical of the formula $-CHR^2CHR^3COOR^4$ wherein $R^2$, $R^3$, and $R^4$ have the same meanings as defined above; m has an average value from 40 to 600; n has an average value of 0 to 100 with the proviso that when n is 0, X denotes Y and (b) from 50 to 100 parts by weight of a physiologically acceptable carrier.

16. The hair treating composition according to claim 15 wherein the anionic surfactant is a sodium, ammonium or triethanolamine salt of lauryl sulfate.

17. The method of conditioning hair which comprises contacting hair with the treating composition defined in claim 15.

* * * * *